US012616789B2

(12) United States Patent
Koh

(10) Patent No.: US 12,616,789 B2
(45) Date of Patent: May 5, 2026

(54) EXTENSIBLE DRUG INJECTION DEVICE AND OPERATION METHOD THEREFOR

(71) Applicant: THE CATHOLIC UNIVERSITY OF KOREA INDUSTRY-ACADEMIC COOPERATION FOUNDATION, Seoul (KR)

(72) Inventor: Hyunjung Koh, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 1185 days.

(21) Appl. No.: 17/616,711

(22) PCT Filed: Jun. 4, 2020

(86) PCT No.: PCT/KR2020/007269
§ 371 (c)(1),
(2) Date: Jul. 18, 2022

(87) PCT Pub. No.: WO2020/246821
PCT Pub. Date: Dec. 10, 2020

(65) Prior Publication Data
US 2022/0362456 A1 Nov. 17, 2022

(30) Foreign Application Priority Data
Jun. 5, 2019 (KR) ........................ 10-2019-0066817

(51) Int. Cl.
*A61M 1/14* (2006.01)
*A61M 5/14* (2006.01)
(Continued)

(52) U.S. Cl.
CPC .......... *A61M 5/1408* (2013.01); *A61M 5/145* (2013.01); *A61M 39/223* (2013.01); *A61M 39/24* (2013.01); *A61M 2005/1406* (2013.01)

(58) Field of Classification Search
CPC ........ A61M 5/1407; A61M 2005/1402; A61M 2005/1403
See application file for complete search history.

(56) References Cited

U.S. PATENT DOCUMENTS 4,411,651 A * 10/1983 Schulman ............. A61M 5/142
417/63
6,017,318 A * 1/2000 Gauthier ............... A61M 39/16
604/258
(Continued)

FOREIGN PATENT DOCUMENTS

JP 2004357985 12/2004
JP 2005143579 6/2005
(Continued)

OTHER PUBLICATIONS

English translation of Nemoto (WO 2014104338) (Year: 2014).*
(Continued)

*Primary Examiner* — Courtney B Fredrickson
(74) *Attorney, Agent, or Firm* — NORTON ROSE FULBRIGHT US LLP

(57) ABSTRACT

The present invention relates to an extensible drug injection device capable of injecting a drug from a location away from a patient, and an operation method therefor. Disclosed is a drug injection device comprising: a first sub-line of which one end joins with a main line, connected from a first drug storage part for storing a first drug to be injected into a patient to the body of the patient such that the first drug flows therein, and of which the other end is extended to the other side; a second drug injection part which is connected to the first sub-line and which injects a second drug that is different
(Continued)

from the first drug; and a second drug pumping part which is connected to the first sub-line, and which pushes, to the main line, the second drug having been injected by the second drug injection part into the first sub-line.

10 Claims, 12 Drawing Sheets

(51) Int. Cl.
    *A61M 5/145*      (2006.01)
    *A61M 39/22*     (2006.01)
    *A61M 39/24*     (2006.01)

(56)            References Cited

U.S. PATENT DOCUMENTS

| | | | |
|---|---|---|---|
| 2002/0045856 A1* | 4/2002 | Jaafar | A61M 5/44 604/113 |
| 2012/0245554 A1* | 9/2012 | Kawamura | A61M 5/142 604/67 |

| | | | |
|---|---|---|---|
| 2013/0253254 A1* | 9/2013 | Uber, III | A61M 5/44 604/82 |
| 2014/0249412 A1* | 9/2014 | Yamamoto | A61M 5/14546 600/432 |

FOREIGN PATENT DOCUMENTS

| | | | | |
|---|---|---|---|---|
| KR | 20110001641 | 2/2011 | | |
| KR | 101888473 | 8/2018 | | |
| KR | 101888473 B1 * | 8/2018 | | A61M 5/165 |
| WO | WO 2009/133705 | 11/2009 | | |
| WO | WO 2014/104338 | 7/2014 | | |
| WO | WO-2014104338 A1 * | 7/2014 | | A61M 5/007 |

OTHER PUBLICATIONS

English Translation of Kim (KR 101888473).*
International Search Report and Written Opinion issued in Corresponding PCT Application No. PCT /KR2020/007269, dated Dec. 4, 2020 (English Translation provided).

* cited by examiner

150

174
176
170
176
172
164
162
160

EXTENSIBLE DRUG INJECTION DEVICE AND OPERATION METHOD THEREFOR

CROSS-REFERENCE TO RELATED APPLICATION

This application is a national phase application under 35 U.S.C. § 371 of International Application No. PCT/KR2020/007269, filed Jun. 4, 2020, which claims priority to and the benefit of Korean Patent Application No. 10-2019-0066817 filed on Jun. 5, 2019, the contents of which applications are incorporated herein by reference in their entirety.

BACKGROUND

Field of the Disclosure

The present invention relates to an extensible drug injection device and an operation method therefor, and more specifically to an extensible drug injection device capable of injecting a drug from a location away from a patient and an operation method therefor.

Description of Related Art

In clinical treatment of patients, a method of administering a medical fluid for the purpose of treatment is frequently applied.

The medical fluid is placed in a bag or bottle containing the medical fluid or drug at a position higher than the patient, and the medical fluid is continuously administered by connecting a medical fluid line to the patient through the medical fluid line.

Meanwhile, when an additional drug or injection solution is to be administered to the patient, a separate line may be connected to the medical fluid line, or the drug may be administered by an injector.

However, this method needs to be carried out in close proximity to the patient, and there is a need for a method of solving this problem because there are cases where it is difficult to access because there are a lot of equipment or medical devices installed around the patient, and where it may be difficult to inject a drug if access is difficult due to the patient's posture or the risk of infection.

SUMMARY OF THE INVENTION

The present invention has been devised in view of the above points, and it is an object of the present invention to provide an extensible drug injection device capable of injecting an additional drug from a location away from a patient.

The problems of the present invention are not limited to the problem mentioned above, and other problems that are not mentioned will be clearly understood by those skilled in the art from the following description.

According to one aspect of the present invention for solving the aforementioned problem, disclosed is a drug injection device, including a first sub-line of which one end joins with a main line, connected from a first drug storage part for storing a first drug to be injected into a patient to the body of the patient such that the first drug flows therein, and of which the other end is extended to the other side, a second drug injection part which is connected to the first sub-line and which injects a second drug that is different from the first drug, and a second drug pumping part which is connected to the first sub-line, and which pushes, to the main line, the second drug having been injected by the second drug injection part into the first sub-line.

The second drug injection part may include a second drug injector for injecting a second drug and a second sub-line for connecting the second drug injector to the first sub-line.

The second drug pumping part may include a pumping solution injector for injecting a pumping solution to push the second drug injected into the first sub-line to the main line, and a third sub-line for connecting the pumping solution injector to the first sub-line.

The drug injection device may further include a pumping solution suction line connected to the third sub-line between a point where the third sub-line is joined to the first sub-line and the pumping solution injector, and supplying a pumping solution suctioned by the pumping solution injector.

The pumping solution suction line may be in communication with the first drug storage part.

One end of the pumping solution suction line connected to the third sub-line may be formed to have a curved end in the third sub-line towards the pumping solution injector.

The third sub-line may be joined with the first sub-line at a point where the second drug injection part is connected to the first sub-line or at a rear side thereof.

The amount of a pumping solution injected by the pumping solution injector at once may be equal to or more than the internal volume of the first sub-line.

The drug injection device may further include a backflow prevention valve provided at one or more points of a point where the first sub-line is connected to the main line, a point where the second drug injection part is connected to the first sub-line, and a point where the second drug pumping part is connected to the first sub-line, and provided such that the flow of the drug or pumping solution flows only towards the main line.

Alternatively, the drug injection device may further include a backflow prevention valve provided in the pumping solution suction line such that the flow of the pumping solution flows only towards the main line.

The backflow prevention valve may include a rim in close contact with an inner circumferential surface of a tube forming the first sub-line to the third sub-line, one or more membranes formed of a flexible material and curved to form at least a portion of a hemisphere while protruding from the rim to a front side in a flow direction of a fluid, and formed to be closed while overlapping each other when the fluid flows in a direction opposite to a flow and to be opened when the fluid flows in a flow direction, and a fine mesh formed on the rim and provided behind the membrane.

The drug injection device may further include a sliding lock valve located in the third sub-line between a point where the third-subline is joined to the first sub-line and a point where the pumping solution suction line is connected, and selectively opening or closing the third sub-line or adjusting the degree of opening.

The sliding lock valve may include a valve body formed with a communication hole connected to a tube of the third sub-line and opened to communicate while facing each other, and a sliding slit formed in a direction orthogonal to the communication hole and having one side opened, and a shutter inserted into the slit to be slid to open or close the communication hole or adjust the degree of opening.

A protrusion having elasticity may be formed at a predetermined interval in one of the sliding slit or the shutter in contact with the sliding sit, and a groove may be formed at an interval corresponding to an interval of the protrusion in the other one of the sliding slit or the shutter in contact with the sliding slit such that the protrusion and the groove are snapped by elasticity.

The shutter may include a slate inserted into the sliding slit to adjust the degree of opening of the communication hole, a handle formed on one side of the slate so as to be exposed from the sliding slit to the outside of the valve body, and a bent part connecting the slate and the handle and provided to be bent on one side.

In addition, the drug injection device may further include a housing for accommodating the second drug injection part and the second drug pumping part.

Meanwhile, disclosed is a method for operating a drug injection device, the drug injection device including a first sub-line of which one end joins with a main line, connected from a first drug storage part for storing a first drug to be injected into a patient to the body of the patient such that the first drug flows therein, and of which the other end is extended to the other side, a second drug injection part which is connected to the first sub-line and which injects a second drug that is different from the first drug, and a second drug pumping part which is connected to the first sub-line, and which pushes, to the main line, the second drug having been injected by the second drug injection part into the first sub-line, and the method includes a second drug injection step in which a piston of the second drug injector is advanced, and the second drug is injected into the first sub-line, a pumping solution loading step in which a piston of the pumping solution injector is retracted, and the pumping solution is loaded into the pumping solution injector, and a pumping step in which a piston of the pumping solution injector is advanced such that the pumping solution in the pumping solution injector is injected into the first sub-line such that the second drug previously injected into the first sub-line is pushed to the main line by the pressure of the pumping solution.

A third sub-line closing step may be performed in which the gap between the first sub-line and the third sub-line is closed prior to the pumping solution loading step.

A third sub-line opening step may be performed in which the gap between the first sub-line and the third sub-line is opened prior to the pumping step.

According to the extensible drug injection device of the present invention and the operation method therefor, it is possible to inject a drug from a location away from a patient, thereby improving the convenience of treatment.

In addition, fine foreign substances such as glass dust and the like in the drug may be filtered, and bubbles in the drug may be finely decomposed to prevent medical accidents such as occlusion by bubbles and the like.

The effects of the present invention are not limited to the above-mentioned effects, and other effects that are not mentioned will be clearly understood by those skilled in the art from the description of the claims.

BRIEF DESCRIPTION OF THE DRAWINGS

The above summary as well as the detailed description of preferred exemplary embodiments of the present application described below may be better understood when read in conjunction with the accompanying drawings. Preferred exemplary embodiments are illustrated in the drawings for the purpose of illustrating the present invention. However, it should be understood that the present application is not limited to the precise arrangement and means illustrated.

DETAILED DESCRIPTION OF THE INVENTION

Figure 1:
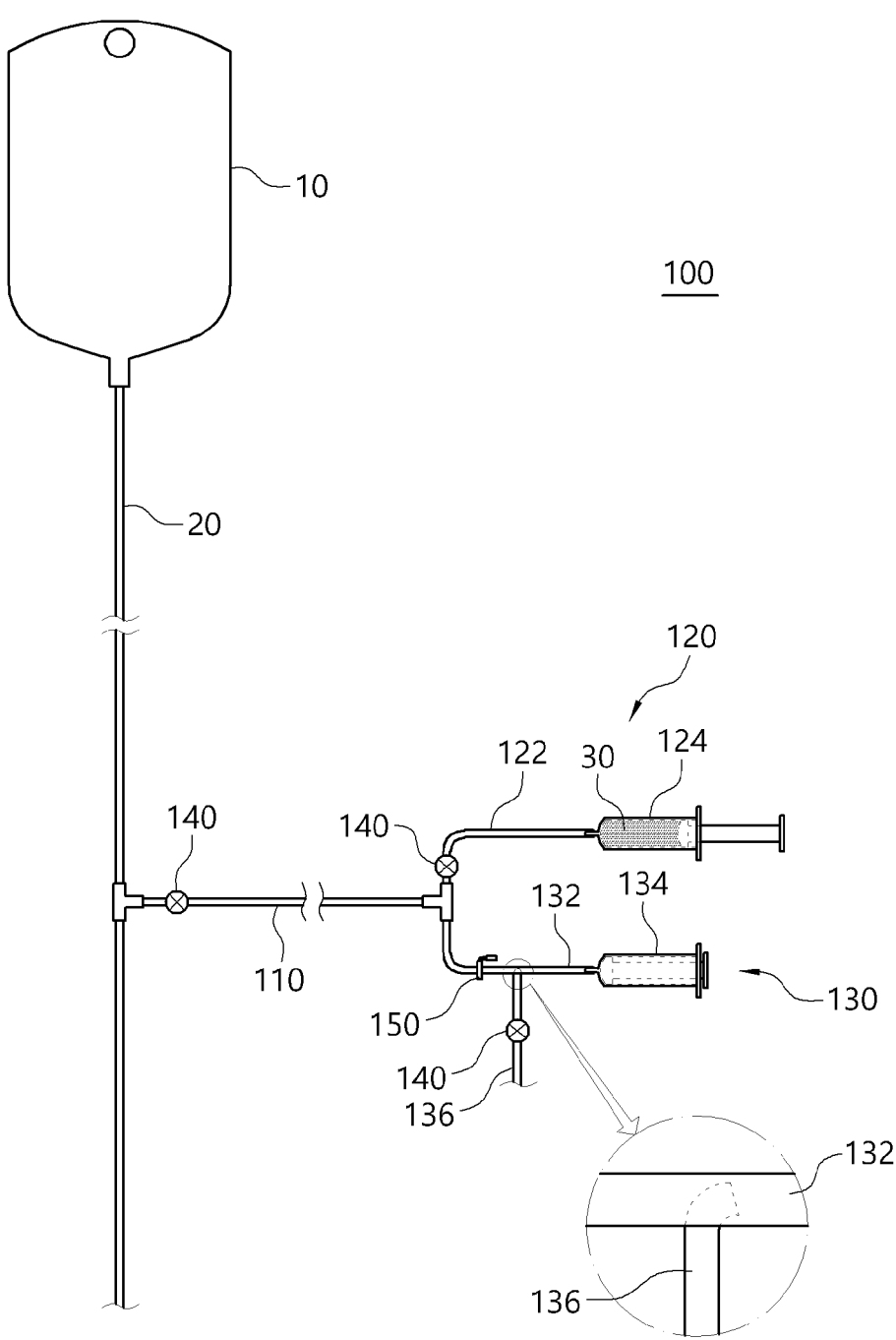
FIGS. 1 to 4 are diagrams illustrating an extensible drug injection device according to an exemplary embodiment of the present invention, which sequentially illustrate a process in which an injection solution and a pumping solution are injected.

Hereinafter, exemplary embodiments of the present invention will be described in detail with reference to the accompanying drawings such that those of ordinary skill in the art to which the present invention pertains may easily practice the present invention. The present invention may be implemented in various different forms, and is not limited to the exemplary embodiments described herein. In the drawings, parts irrelevant to the description are omitted in order to clearly describe the present invention, and the same reference numerals are added to the same or similar components throughout the specification.

The extensible drug injection device 100 according to the present exemplary embodiment may include a first sub-line 110, a second drug injection part 120 and a second drug pumping part 130, as illustrated in FIGS. 1 to 4.

In order to continuously administer a medical liquid, a drug or the like to a patient, a medical liquid set may be used.

Such a medical liquid set may include a first drug storage part 10 in which a first drug to be administered to a patient is stored, a main line 20 connected to the patient from the first drug storage part 10 and through which the first drug flows, and a catheter (not illustrated) provided at an end of the main line 20 and inserted into the patient.

The first drug storage part 10 may be composed of a material such as a bag, a glass bottle or the like made of vinyl or PE, and it may be provided to be mounted at a position higher than the patient to supply a first drug by gravity.

In addition, in the extensible drug injection device 100 of the present exemplary embodiment, one end of the first sub-line 110 may be laminated to a middle of the main line 20, and the other end of the first sub-line 110 may be made of a flexible soft tube made of silicon or PE extended to the other side.

The second drug injection part 120 is connected to the first sub-line 110, and it is a component for injecting a second drug 30 having a component different from the first drug into the first sub-line 110.

In addition, the second drug pumping part 130 is connected to the first sub-line 110, and it is a component for pushing the second drug 30 injected into the first sub-line 110 by the second drug injection part 120 to the main line 20.

As illustrated in FIG. 1, the second drug injection part 120 may include a second drug injector 124 and a second sub-line 122.

The second drug 30 may be contained in the second drug injector 124. The second drug 30 may be the same component as the first drug or may be a drug having a different component. In addition, the second sub-line 122 may be connected from the second drug injector 124 to the first sub-line 110 to be joined to the first sub-line 110, and may serve as a passage for guiding the second drug 30 of the second drug injector 124 to the first sub-line 110.

The second drug injector 124 may be detachably provided to the second sub-line 122, and may be provided to fill a drug while being removed from the second sub-line 122 when filling the drug in the second drug injector 124.

The second drug pumping part 130 may include a pumping solution injector 134 and a third sub-line 132.

The pumping solution injector 134 is a component for injecting a pumping solution 40, which pushes the second drug 30 injected into the first sub-line 110 to the main line 20, to the first sub-line 110.

In addition, the third sub-line 132 may be connected from the pumping solution 40 injector to the first sub-line 110 to serve as a passage for guiding a pumping solution 40 of the pumping solution injector 134 to the first sub-line 110.

The pumping solution 40 is a drug that serves to push the second drug 30 to the main line 20, and it may be a drug that is harmless to the human body or may assist in treatment.

The pumping solution 40 may be the same drug as the first drug or the second drug 30, or may be a drug that is harmless to the human body, such as physiological saline and the like. Alternatively, the pumping solution 40 may be a drug having a different component from the first drug and the second drug 30.

Accordingly, the pumping solution 40 may be injected from the pumping solution injector 134 to the first sub-line 110 through the third sub-line 132.

Meanwhile, a pumping solution suction line 136 may be further provided such that the pumping solution 40 may be filled in the pumping solution injector 134 even when the pumping solution injector 134 is not separated from the third sub-line 132.

One end of the pumping solution suction line 136 may be coupled to the third sub-line 132, and the other end of the pumping solution suction line 136 may extend to the other side so as to be connected to a storage in which the pumping solution 40 is stored.

The storage in which the pumping solution 40 is stored may be any storage in which the pumping solution 40 is contained.

That is, when the first drug is applied as the pumping solution 40, the pumping solution suction line 136 may be connected to a first drug storage part 10.

Alternatively, the pumping solution suction line 136 may not be connected to the first drug storage part 10 but may be connected to another drug storage part.

In addition, one end of the pumping solution suction line 136 coupled to the third sub-line 132 may be curved such that the end of the pumping solution suction line 136 faces the pumping solution injector 134 in the third sub-line 132. This is to allow the pumping solution 40 introduced into the third sub-line 132 through the pumping solution suction line 136 to flow directly towards the pumping solution injector 134 without flowing towards the first sub-line 110.

Meanwhile, a point where the third sub-line 132 is joined to the first sub-line 110 may be the same as a point where the second drug injection part 120 is connected to the first sub-line 110 or may be a rear side thereof.

In the first sub-line 110 to the third sub-line 132, a direction of flowing from the second drug injector 124 or the pumping solution injector 134 towards the main line 20 is defined as a front side, and the rear side means to be in the opposite direction of the front side.

Accordingly, the pumping solution 40 injected into the first sub-line 110 through the third sub-line 132 may push the second drug 30 injected into the first sub-line 110 through the second sub-line 122 from the rear side to the front side.

In addition, the amount of the pumping solution 40 injected by the pumping solution injector 134 at once may be equal to or more than the internal volume of the first sub-line 110. Therefore, even with a single injection of the pumping solution 40, all of the injected second drug 30 may be pushed up to the main line 20.

Herein, although it is generally advantageous if the second sub-line 122 and the third sub-line 132 are short in length, the present invention does not particularly limit the lengths of the second sub-line 122 and the third sub-line 132, and the lengths of the second sub-line 122 and the third sub-line 132 may be increased or decreased as necessary.

Figure 5:
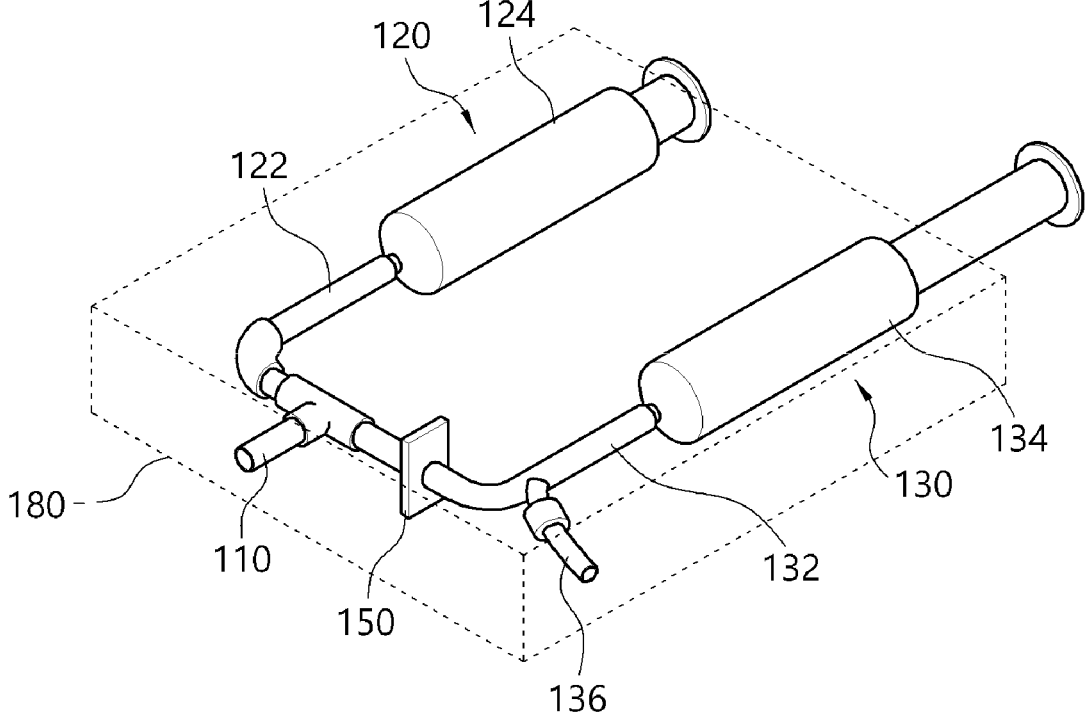
FIG. 5 is a perspective view illustrating a state in which a second drug injection part and a second drug pumping part of the extensible drug injection device are provided inside a housing.

In addition, as illustrated in FIG. 5, the second drug injection part 120 and the second drug pumping part 130 may be provided inside a housing 180.

In addition, a tube of the first sub-line 110 may be coupled to any one side of the housing 180. In addition, a tube connected to the pumping solution suction line 136 may be coupled to any one side of the housing 180.

The second drug injector 124 and the pumping solution injector 134 may have cylinders located inside the housing 180, and only pistons may be exposed to the outside of the housing 180.

Figure 6:
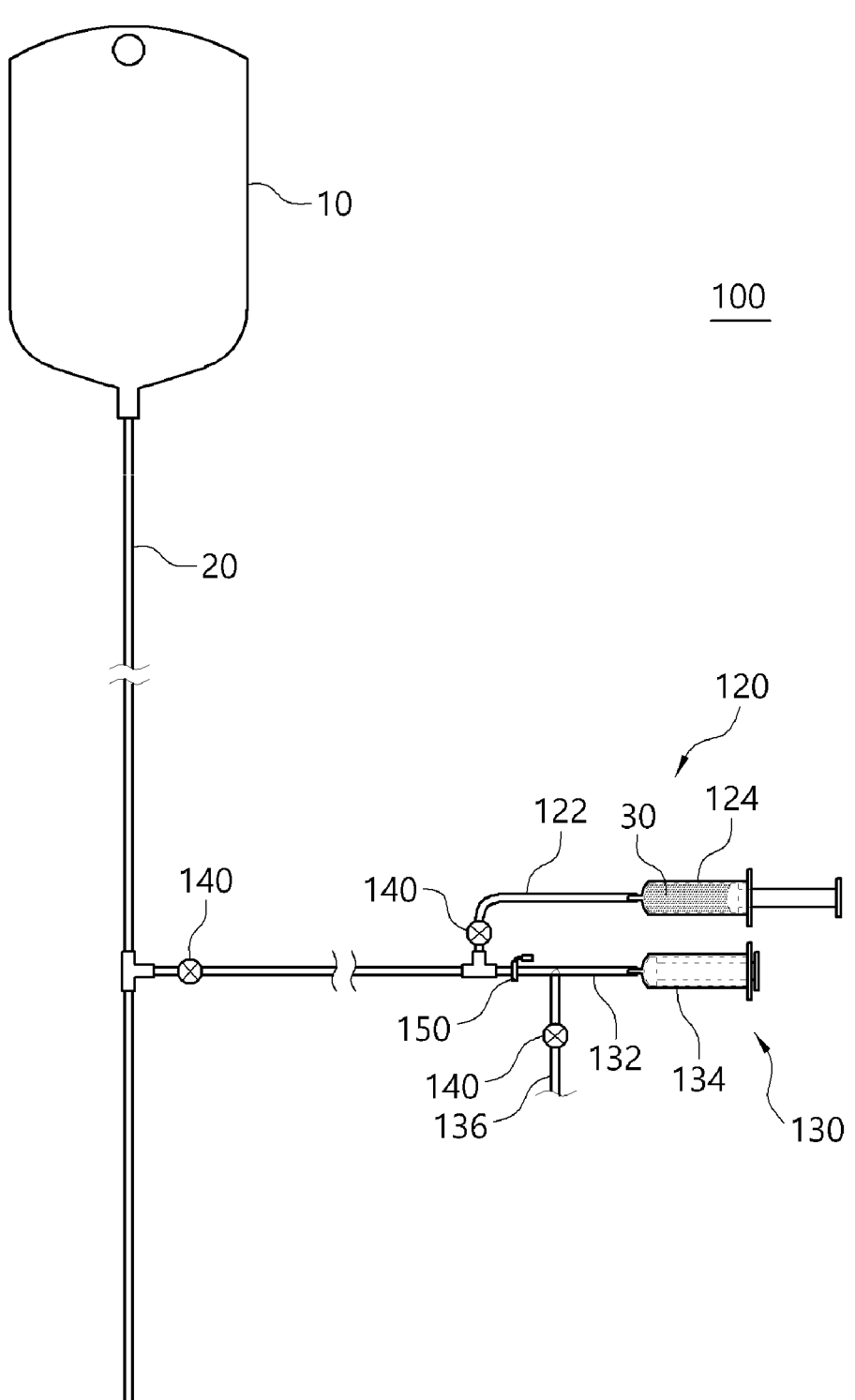
FIG. 6 is a diagram illustrating an extensible drug injection device according to another exemplary embodiment of the present invention.

FIG. 6 is a diagram illustrating another exemplary embodiment of an extensible drug injection device 100 of the present invention.

The extensible drug injection device 100 according to the present exemplary embodiment is the same as the extensible drug injection device 100 of the above-described exemplary embodiment, but the third sub-line 132 is not separately provided, and it may be formed in a structure in which the third sub-line 132 is integrally formed with the first sub-line 110 at the end of the first sub-line 110.

That is, the first sub-line 110 is elongated to perform the function of the third sub-line 132, and the second sub-line 122 is laminated to a middle of the first sub-line 110.

Figure 2:
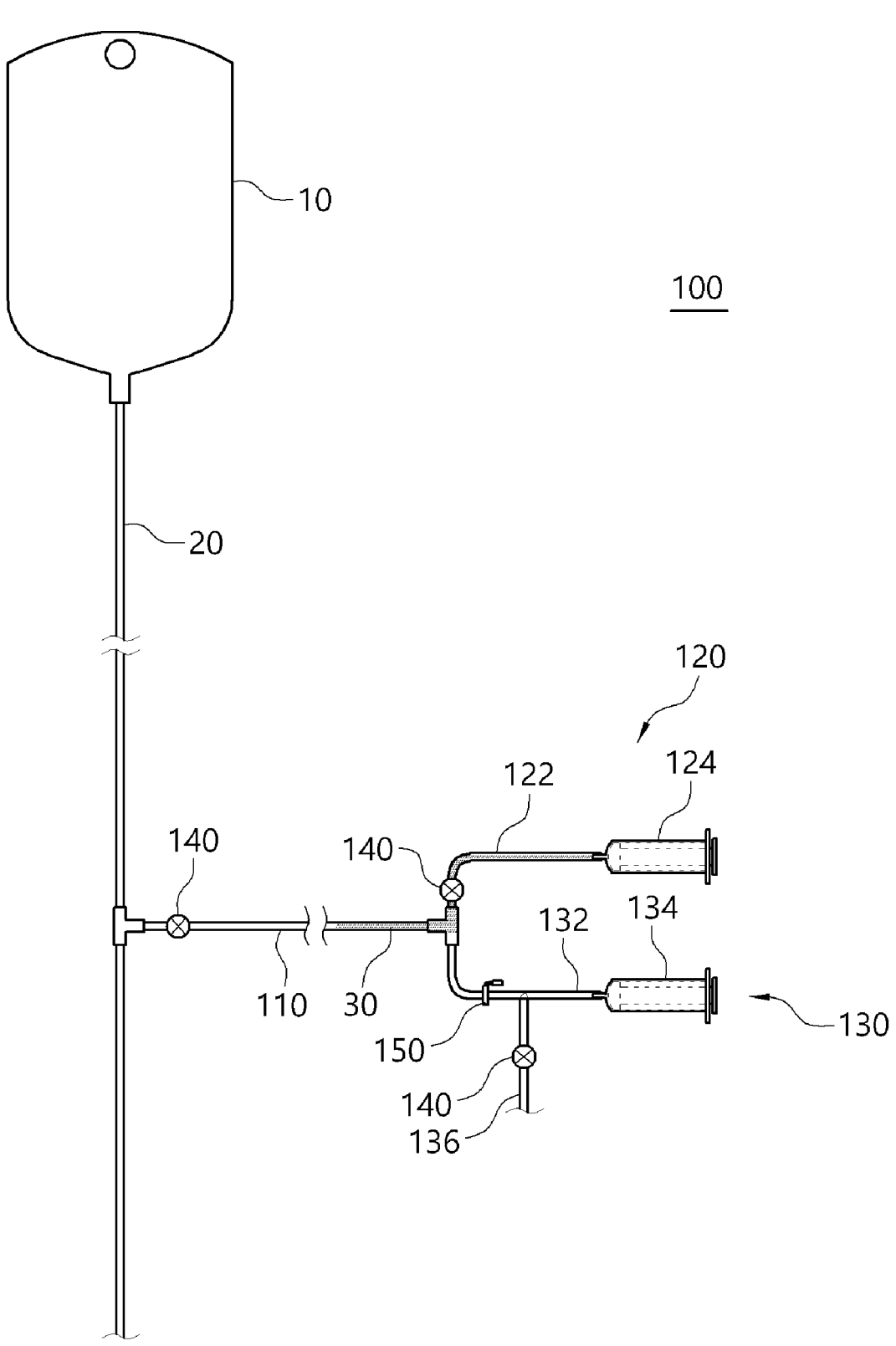

Accordingly, as illustrated in FIG. 1, after the second drug injector 124 filled with the second drug 30 is provided, as illustrated in FIG. 2, when the piston of the second drug injector 124 is pushed and advanced, the second drug 30 may enter the first sub-line 110 through the second sub-line 122.

Although the amount of the second drug 30 may vary depending on the length of the first sub-line 110, the amount of a drug injected into an injector is generally about several cc, and thus, the injected second drug 30 may not enter the main line 20 and may stay after entering the first sub-line 110.

Figure 3:
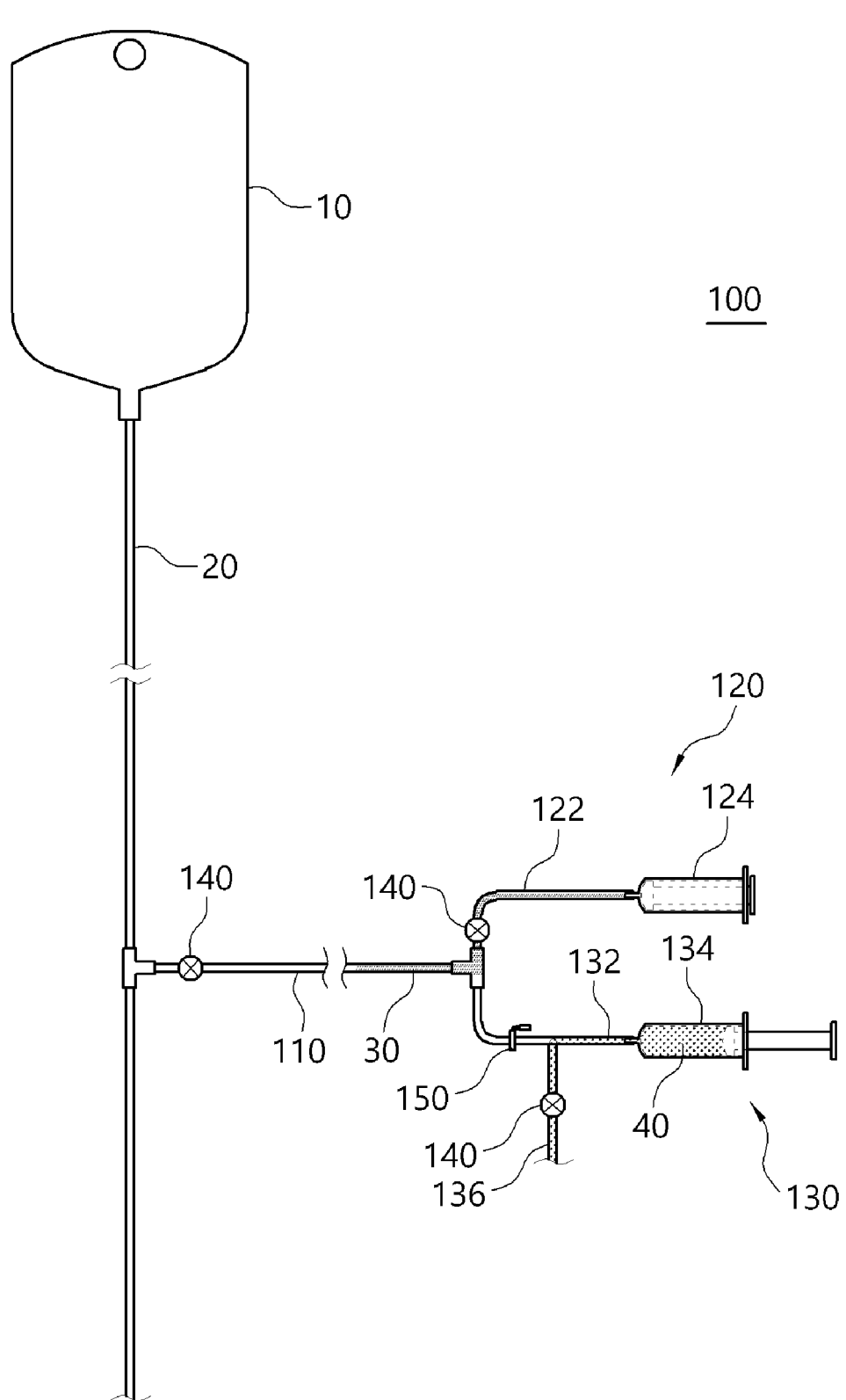

In this case, as illustrated in FIG. 3, the piston of the pumping solution injector 134 of the second drug pumping part 130 may be retracted to suction the pumping solution 40 into the pumping solution injector 134 through the pumping solution suction line 136.

Figure 4:
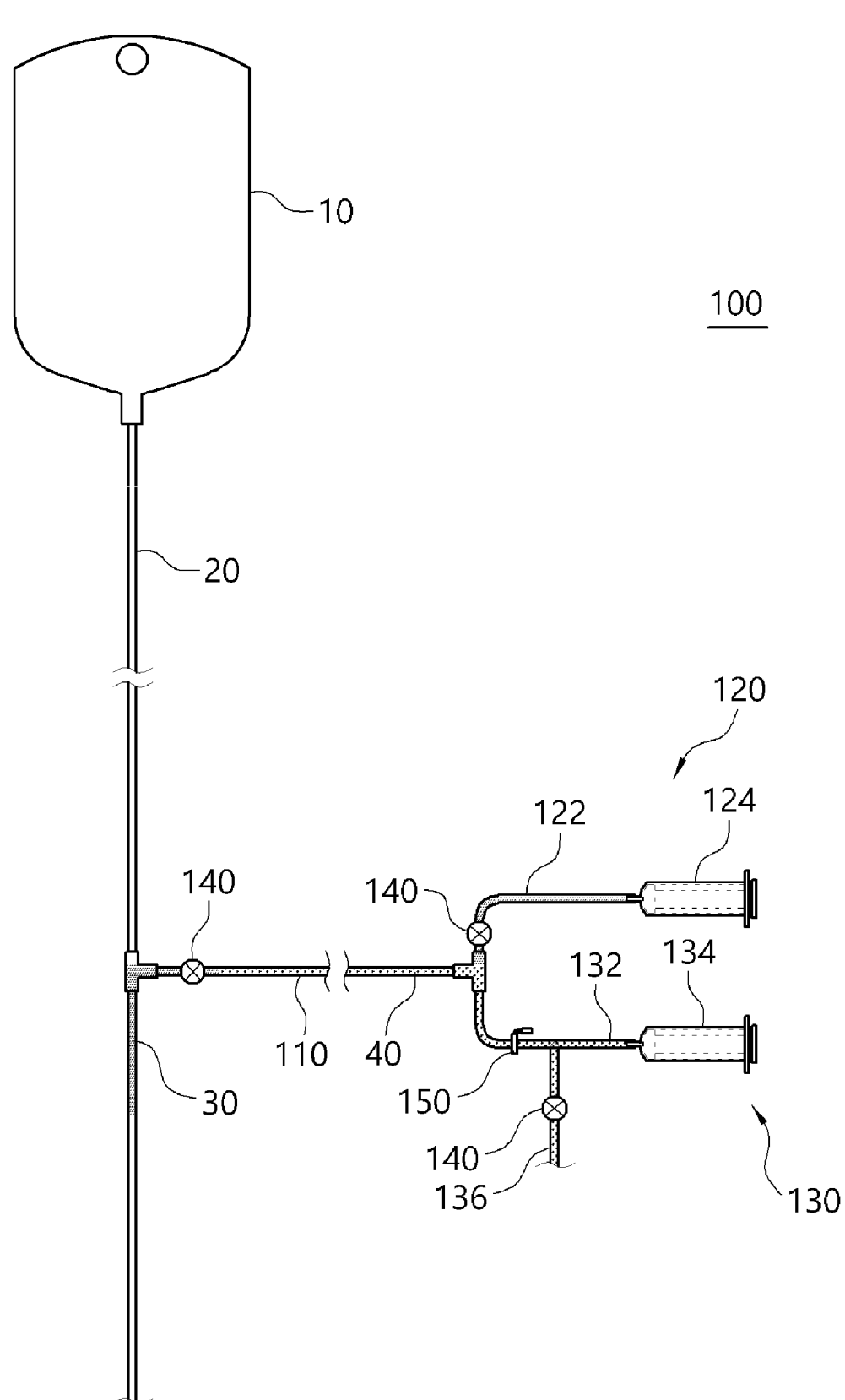

Further, as illustrated in FIG. 4, when the piston of the pumping solution injector 134 is advanced, the pumping solution 40 in the pumping solution injector 134 may enter the first sub-line 110 through the third sub-line 132 so as to push the second drug 30 remaining in the first sub-line 110 towards the main line 20.

The second drug 30 that has entered the main line 20 may be administered to the body of the patient together with the first drug that has already flown through the main line 20.

Meanwhile, a backflow prevention valve 140 may be provided. The backflow prevention valve 140 is a component that allows the second drug 30 and the pumping solution 40 to flow forward only in one direction and prevents the second drug 30 and the pumping solution 40 from flowing in the opposite direction, and may be provided at one or more or all of a point where the first sub-line 110 is connected to the main line 20, a point where the second drug injection part 120 is connected to the first sub-line 110, a point where the second drug pumping part 130 is connected to the first sub-line 110, and the pumping solution suction line 136.

Figure 7:
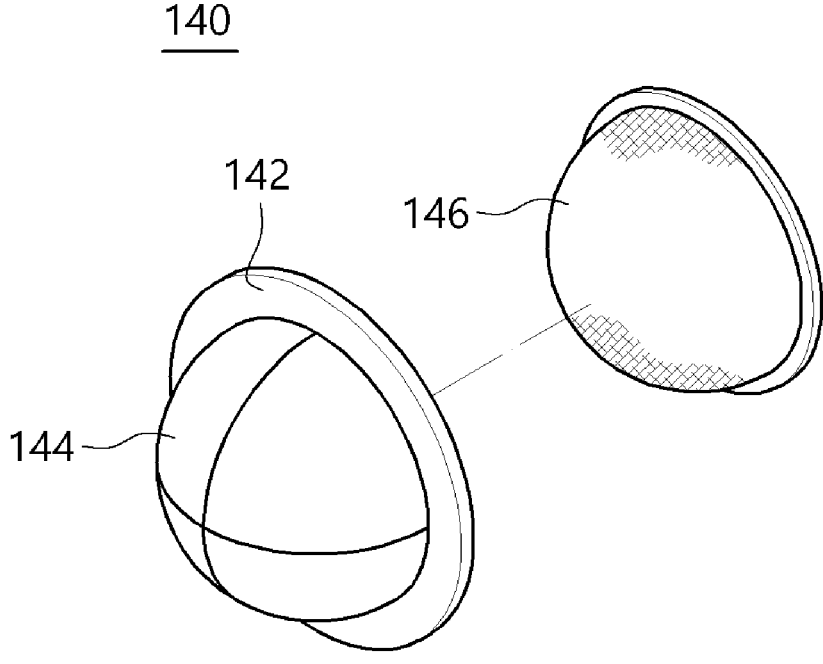
FIG. 7 is an exploded perspective view illustrating a backflow prevention valve provided in the extensible drug injection device according to an exemplary embodiment of the present invention.
Figure 8:
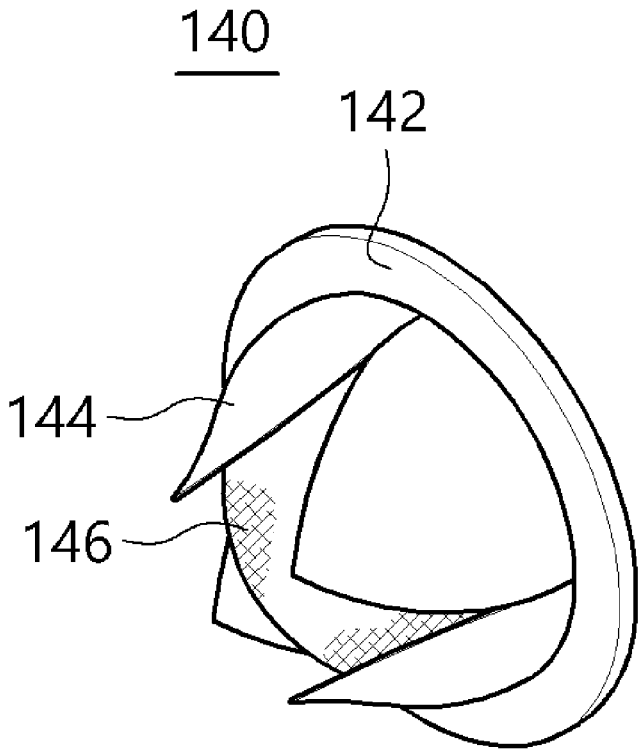
FIG. 8 is a perspective view illustrating a state in which the backflow prevention valve of FIG. 7 is opened while being coupled.

As illustrated in FIGS. 7 and 8, the backflow prevention valve 140 may include a rim 142 closely contacting an inner circumferential surface of a tube forming the first sub-line 110 to the third sub-line 132, and at least one membrane 144 and a fine mesh 146 formed on the rim 142.

The membrane 144 may be formed of a flexible material, protrude from the rim 142 to the front side in a flow direction of a fluid and be curved to form at least a portion of a hemisphere, and it may overlap and close when the fluid flows in a direction opposite to the flow direction, and open when the fluid flows in a flow direction.

In addition, the fine mesh 146 may be formed inside the rim 142, located at a rear side of the membrane 144, and form a hemisphere similar to the membrane 144.

Accordingly, when the second drug 30 and the pumping solution 40 flow towards the front side, the membrane 144 may be opened as illustrated in FIG. 8, and when the second drug 30 and the pumping solution 40 flow in opposite directions, the membrane 144 may be closed to block the flow of the second drug 30 and the pumping solution 40 in the reverse direction as illustrated in FIG. 7. In this case, the fine mesh 146 may support the membrane 144 so as to prevent the membrane 144 from being wetted towards the rear side and being opened.

In addition, the fine mesh 146 may perform a function of filtering foreign substances included in the second drug 30, the pumping solution 40 and the like in addition to a function of supporting the membrane 144. Moreover, when bubbles are included in the second drug 30 or the pumping solution 40, the bubbles may be finely decomposed to prevent occlusion that may occur when the bubbles flow into the blood vessel.

Further, a sliding locking valve 150 may be provided. The sliding locking valve 150 is provided in the third sub-line 132 to be a component for selectively opening and closing the third sub-line 132 or adjusting the degree of opening, and it may be provided in the third sub-line 132 between a point where the third sub-line 132 is joined with the first sub-line 110 and a point where the pumping solution suction line 136 is coupled.

Figure 9:
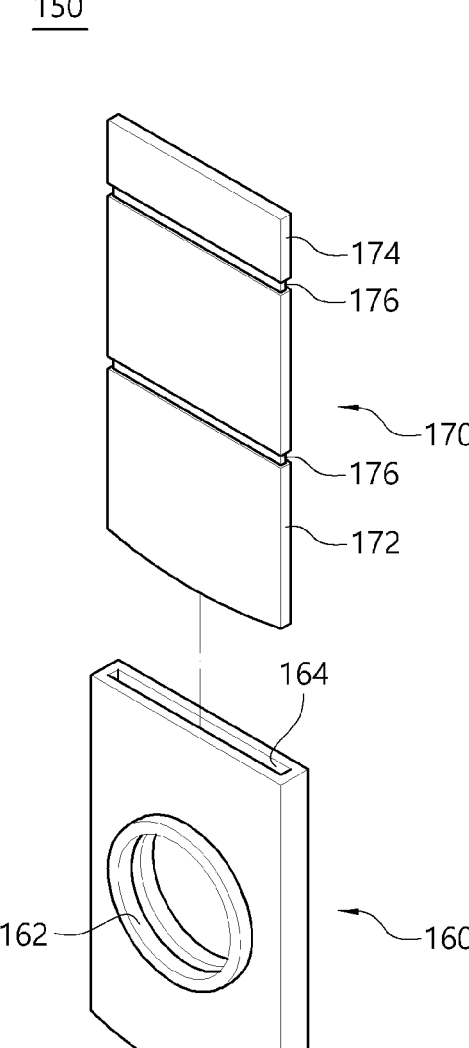
FIG. 9 is a perspective view illustrating a sliding lock valve provided in the extensible drug injection device according to an exemplary embodiment of the present invention.
Figure 10:
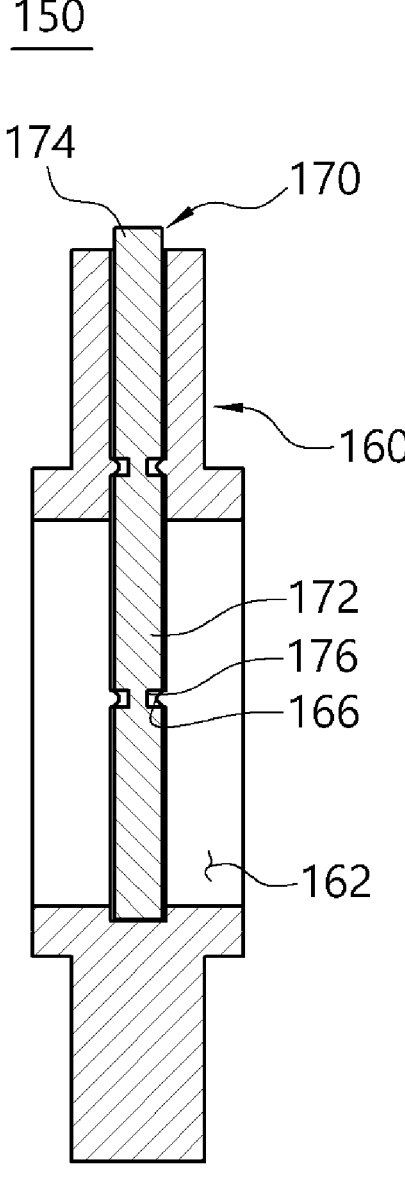
FIG. 10 is a cross-sectional view illustrating a state in which the sliding lock valve of FIG. 9 is closed.
Figure 11:
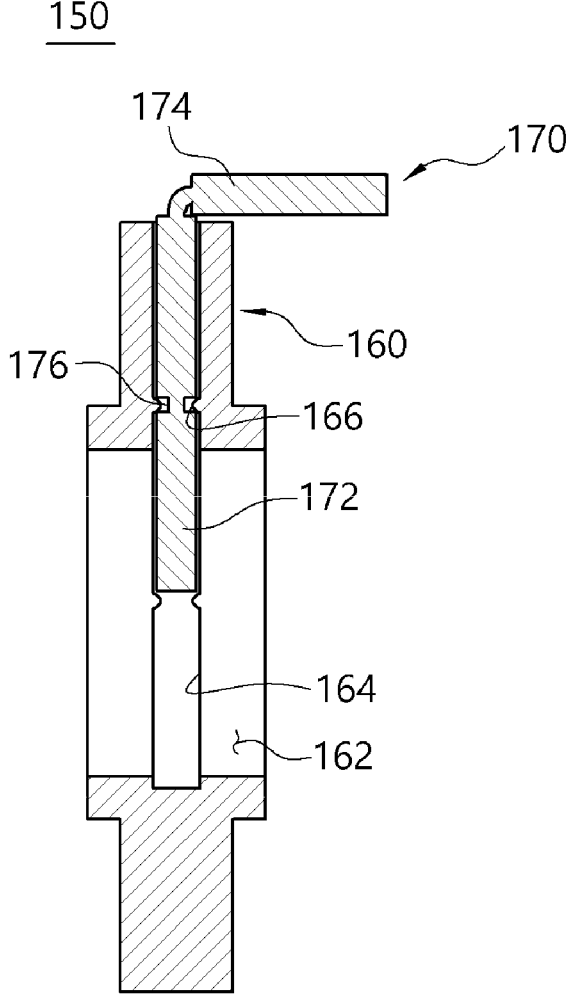
FIG. 11 is a cross-sectional view illustrating a state in which the sliding lock valve of FIG. 9 is partially opened.

As illustrated in FIGS. 9 to 11, the sliding locking valve 150 may include a valve body 160 and a shutter 170.

The valve body 160 may be formed with a communication hole 162 to which a tube of the third sub-line 132 is connected and opened to communicate while facing each other, and a sliding slit 164 formed in a direction and a depth orthogonal to the communication hole 162 and having one side opened.

Further, the shutter 170 may be formed in a plate shape to be inserted into the sliding slit 164 so as to be slid to open and close the communication hole 162 or adjust the degree of opening.

In addition, one or a plurality of elastic protrusions 166 may be formed at a predetermined interval in one of the sliding slit 164 or the shutter 170 in contact with the sliding slit 164, and a groove 176 may be formed at an interval corresponding to an interval of the protrusion 166 in the other one of the sliding slit 164 or the shutter 170 in contact with the sliding slit 164.

Accordingly, the protrusion 166 may be elastically inserted into the groove 176 and snap-fastened to elastically fix a position thereof, and accordingly, as illustrated in FIG. 10, the communication hole 162 may be maintained in a closed state, or as illustrated in FIG. 11, the communication hole 162 may be maintained in a partially open state. Certainly, the communication hole 162 may be completely opened as necessary.

Meanwhile, the shutter 170 may include a slate 172 inserted into the sliding slit 164 to adjust the degree of opening of the communication hole 162 and a handle 174 provided at one side of the slate 172 so as to be exposed from the sliding slit 164 to the outside of the valve body 160.

Accordingly, the protrusion 166 or the groove 176 is formed in the slate 172, and the slate 172 may open or close the communication hole 162 while sliding inside the sliding slit 164.

The user may adjust the position of the slate 172 by holding and pushing or pulling the handle 174.

Meanwhile, the handle 174 protrudes to the outside of the valve body 160 so to be held by the user, and thus, the handle 174 that protrudes to the outside may be caught in another tube or somewhere to interfere with the handle 174. Therefore, in order to avoid such inconvenience, a bent part 177 may be provided between the handle 174 and the slate 172.

The bent part 177 connects the slate 172 and the handle 174 and is provided to be bendable to one side, and after the operation of adjusting the degree of opening of the shutter 170 is finished, the handle 174 is bent as illustrated in FIG. 11, thereby minimizing a phenomenon of being caught in somewhere to interfere with the handle 174, and simultaneously preventing the movement, thereby maintaining the adjustment of the degree of opening of the shutter 170.

The bent part 177 may be formed of a lead and a coating, and the lead may be formed of a metal material having ductility, and one end thereof may extend to the slate 172, and the other end thereof may extend to the handle 174.

In addition, the coating may form an outer shell of the lead such that the lead is not exposed to the outside.

Certainly, it is possible to select as necessary whether the sliding locking valve 150 is selectively provided.

Hereinafter, an exemplary embodiment of the method for operating the extensible drug injection device of the present invention will be described.

Figure 12:
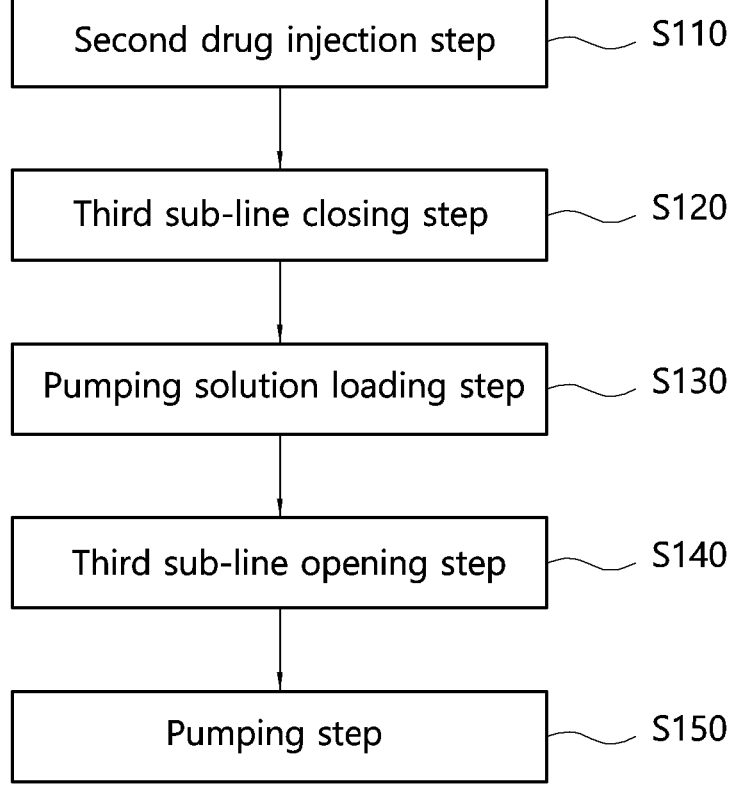
FIG. 12 is a flowchart illustrating a method for operating the extensible drug injection device of the present invention.

As illustrated in FIG. 12, the method for operating the extensible drug injection device 100 according to the present exemplary embodiment may include a second drug injection step S110, a third sub-line closing step S120, a pumping solution loading step S130, a third sub-line opening step S140 and a pumping step S150.

As illustrated in FIG. 1, the second drug injection step S110 is a step in which the second drug injector 124 filled with the second drug 30 is provided, and then, as illustrated in FIG. 2, a piston of the second drug injector 124 is advanced such that the second drug 30 is injected into the first sub-line 110 through the second sub-line 122.

In this case, although it may vary depending on the amount of the second drug 30 and the length of the first sub-line 110, the amount of a drug injected into an injector is generally about several cc, and the injected second drug 30 may not enter the main line 20 and may remain after entering the first sub-line 110.

The third sub-line closing step S120 may be a step in which the third sub-line 132 is closed by closing the communication hole 162 by the shutter 170 of the sliding lock valve 150. The pumping solution loading step S130 may be performed after the third sub-line closing step S120. As illustrated in FIG. 3, the pumping solution loading step S130 is a step in which a piston of the pumping solution injector 134 of the second drug pumping part 130 is retracted such that the pumping solution 40 is loaded into the pumping solution injector 134 through the pumping solution suction line 136. In this case, while a negative pressure to flow in the backward direction is formed in the third sub-line 132, the third sub-line 132 is closed through the third sub-line closing step S120, and the second drug 30 in the first sub-line 110 and the second sub-line 122 may not flow into the third sub-line 132 by the backflow prevention valve 140 installed in a plurality of places, and the pumping solution 40 may be loaded only through the pumping solution suction line 136.

After the pumping solution loading step S130, the third sub-line opening step S140 may be performed. The third sub-line opening step S140 may be a step in which the third sub-line 132 is opened by opening the communication hole 162 through the shutter 170 of the sliding lock valve 150.

After the third sub-line opening step S140, the pumping step S150 may be performed. As illustrated in FIG. 4, the pumping step S150 is a step in which a piston of the pumping solution injector 134 is advanced, and the pumping solution 40 in the pumping solution injector 134 is injected into the first sub-line 110 through the third sub-line 132, and the second drug 30 remaining in the first sub-line 110 is pushed towards the main line 20 by a pressure thereof.

The second drug 30 injected into the main line 20 may be administered to the body of the patient together with the first drug already flowing in the main line 20.

Although an exemplary embodiment of the present invention has been described above, the spirit of the present invention is not limited to the exemplary embodiment presented in the present specification, and those skilled in the art who understand the spirit of the present invention will be able to easily suggest other exemplary embodiments by modifying, changing, deleting or adding components within the scope of the same spirit, but this is also said to be within the scope of the present invention.

The invention claimed is:

1. A drug injection device, comprising:
a first sub-line of which a first end joins with a main line, connected from a first drug storage part for storing a first drug to be injected into a body of a patient such that the first drug flows therein; a second drug injection part which is connected to a second end of the first sub-line and is configured to apply pressure to inject a second drug that is different from the first drug; and a second drug pumping part which is connected to the first sub-line, and is configured to apply pressure to push the second drug which has been injected into the first sub-line by the second drug injection part toward the main line,
wherein the second drug pumping part comprises:
a pumping solution injector for injecting a pumping solution to push the second drug into the main line;
a third sub-line for connecting the pumping solution injector to the first sub-line;
a pumping solution suction line branched from the third sub-line at a location between the pumping solution injector and a junction where the third sub-line joins with the first sub-line, the pumping solution suction line defining a flow path for supplying a pumping solution to be sucked into the pumping solution injector; and
a sliding lock valve located on the third sub-line between the junction where the third sub-line joins with the first sub-line and a point where the pumping solution suction line is coupled, wherein the sliding lock valve comprises:
a valve body including a communication hole which is open at both ends to be connected to a tube of the third sub-line and defines a fluid passage through the valve body, and a sliding slit formed in a direction intersecting the communication hole; and
a shutter disposed within the sliding slit and configured to block a fluid flow or regulate a flow rate through the communication hole according to a sliding movement of the shutter,
wherein a protrusion having elasticity is formed at a predetermined interval in one of the sliding slit or the shutter in contact with the sliding slit, and a groove is formed at an interval corresponding to the predetermined interval of the protrusion in the other one of the sliding slit or the shutter in contact with the sliding slit such that the protrusion and the groove are snapped by elasticity.

2. The drug injection device of claim 1, wherein the second drug injection part comprises:
a second drug injector for injecting the second drug; and
a second sub-line for connecting the second drug injector to the first sub-line.

3. The drug injection device of claim 1, wherein the pumping solution suction line is in communication with the first drug storage part.

4. The drug injection device of claim 1, wherein one end of the pumping solution suction line connected to the third sub-line is formed to have a curved end in the third sub-line towards the pumping solution injector.

5. The drug injection device of claim 1, wherein the third sub-line is joined with the first sub-line at a point where the second drug injection part is connected to the first sub-line or at a rear side thereof.

6. The drug injection device of claim 1, wherein an amount of the pumping solution injected by the pumping solution injector at once is equal to or more than an internal volume of the first sub-line.

7. The drug injection device of claim 1, further comprising a backflow prevention valve disposed at any one point selected from a point where the first sub-line is connected to the main line, a point where the second drug injection part is connected to the first sub-line, or a point where the second drug pumping part is connected to the first sub-line, wherein the backflow prevention valve is configured to restrict a flow of the drug or pumping solution.

8. The drug injection device of claim 7, wherein the backflow prevention valve comprises:

a rim in close contact with an inner circumferential surface of a tube forming the first sub-line to the third sub-line;

one or more membranes formed of a flexible material and curved to form at least a portion of a hemisphere while protruding from the rim to a front side in a flow direction of a fluid, and formed to be closed while overlapping each other when the fluid flows in a direction opposite to a flow and to be opened when the fluid flows in a flow direction; and a fine mesh formed on the rim and provided behind the membrane.

9. The drug injection device of claim 1, wherein the shutter comprises:

a slate inserted into the sliding slit to adjust a degree of opening of the communication hole;

a handle formed on one side of the slate so as to be exposed from the sliding slit to the outside of the valve body; and a bent part connecting the slate and the handle and provided to be bent on one side.

10. The drug injection device of claim 1, further comprising a housing for accommodating the second drug injection part and the second drug pumping part.

\* \* \* \* \*